United States Patent [19]

Spivack

[11] 4,081,475
[45] Mar. 28, 1978

[54] TRIALKYLSUBSTITUTED HYDROXYBENZYL MALONATES AND STABILIZED COMPOSITIONS

[75] Inventor: John D. Spivack, Spring Valley, N.Y.

[73] Assignee: Ciba-Geigy Corporation, Ardsley, N.Y.

[21] Appl. No.: 596,865

[22] Filed: Jul. 17, 1975

Related U.S. Application Data

[63] Continuation of Ser. No. 423,347, Dec. 10, 1974, abandoned.

[51] Int. Cl.$^2$ ............................................. C07C 69/76
[52] U.S. Cl. .............................. 560/55; 260/45.85 B; 260/570.9; 260/630 D
[58] Field of Search ..................................... 260/473 S

[56] References Cited

U.S. PATENT DOCUMENTS

| Re. 27,004 | 12/1970 | Meier et al. ........................ 260/473 S |
| 3,450,746 | 6/1969 | Stapfer .............................. 260/473 S |
| 3,542,728 | 11/1970 | Gersmann et al. ................... 260/473 |
| 3,646,110 | 2/1972 | Eggensperger et al. ........... 260/473 S |
| 3,663,596 | 5/1972 | Gersmann et al. ............... 260/473 X |
| 3,678,095 | 7/1972 | Dexter et al. ..................... 260/473 S |
| 3,721,704 | 3/1973 | Dexter ............................... 260/473 S |

FOREIGN PATENT DOCUMENTS 1,936,280   1/1970   Germany .......................... 260/473 S Primary Examiner—Paul J. Killos
Attorney, Agent, or Firm—Nestor W. Shust

[57] ABSTRACT

Compounds having the formula

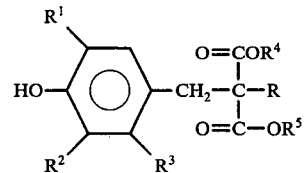

wherein
R$^1$, R$^2$ and R$^3$ are alkyl or cycloalkyl;
R$^4$ and R$^5$ are alkyl or phenyl; and
R is hydrogen, alkyl or a trialkylhydroxybenzyl, are good antioxidants and thermal stabilizers. These compounds are prepared by reacting the corresponding alkylated 4-hydroxybenzyl-tert-amine with a malonate ester in the presence of an alkali metal alkoxide.

7 Claims, No Drawings

TRIALKYLSUBSTITUTED HYDROXYBENZYL MALONATES AND STABILIZED COMPOSITIONS

This is a continuation of application Ser. No. 423,347 filed on Dec. 10, 1974, now abandoned.

DETAILED DISCLOSURE

This invention pertains to trialkyl-substituted 4-hydroxybenzyl malonates and to organic materials normally subject to oxidative and thermal degradation stabilized with said malonates. The compounds of this invention can be represented by the formula

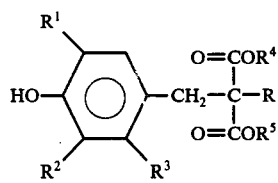

wherein

R$^1$, R$^2$ and R$^3$ are independently alkyl groups of 1 to 8 carbons or cycloalkyl of 5 or 6 carbons provided that no more than 2 cycloalkyl groups are present, R$^4$ and R$^5$ are alkyl of 1 to 30 carbons, phenyl or alkyl substituted phenyl having up to 24 carbons, and R is hydrogen, alkyl of 1 to 8 carbons or a group

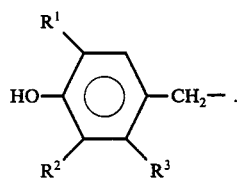

The R$^1$, R$^2$ and R$^3$ groups can be straight or branched lower alkyl groups having 1 to 8 carbon atoms as for example, methyl, ethyl, propyl, butyl, pentyl, heptyl or octyl. Preferably R$^1$ is a branched alkyl group such as isopropyl, sec-butyl, tert-butyl, sec and tert-pentyl, sec- and tert-hexyl, sec- and tert-heptyl or sec- and tert-octyl and most preferably a tert-butyl group. R$^2$ and R$^3$ are preferably an alkyl group having 1 to 3 carbon atoms and most preferably methyl. R$^1$ is preferably a branched alkyl and most preferably tert-butyl. Preferably R$^4$ and R$^5$ are alkyl of 1 to 18 carbons and R is hydrogen or the trialkyl 4-hydroxybenzyl group represented above.

Compounds of the invention are made by reacting the corresponding alkylated 4-hydroxybenzyltertiary amine of the formula Ib

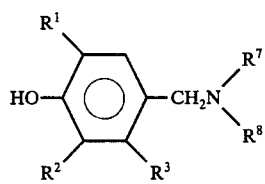

where R$^7$ and R$^8$ are alkyl, R$^7$ and R$^8$ together with the nitrogen atom may also be a morpholine or piperidine ring with the appropriate malonate ester of structure Ic preferably in the presence of an alkali metal alkoxide, amide, or hydride.

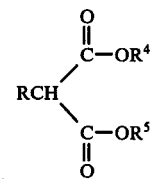

where the symbols are as defined in formula I.

The stabilizers of this invention are thus mono(alkylhydroxybenzyl)malonate or bis (alkylhydroxybenzyl)malonates depending on the definition of R as detailed in formula I above.

For example, when R is hydrogen or alkyl mono(alkylhydroxybenzyl)malonate stabilizers are made as shown in reaction (1) preferably in the presence of an alkali metal alkoxide, amide or hydride, the product being isolated after acidification.

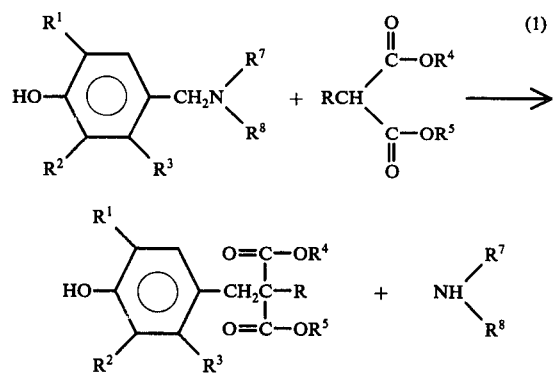

On the other hand, when R is an alkyl hydroxybenzyl group as shown in I, stabilizers of this invention are made as shown in equation (2) using an alkali metal alkoxide or hydride to catalyze the reaction.

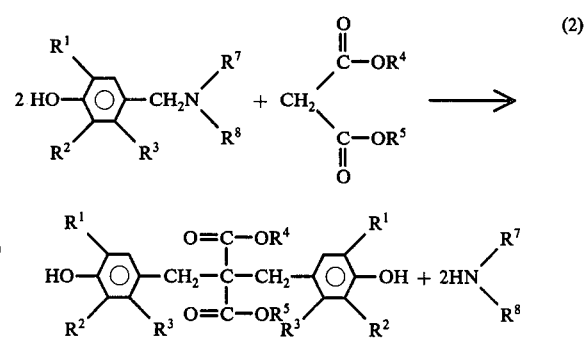

Alternatively alkylhydroxybenzyl halides of formula II may be employed in an analogous manner for reaction with the appropriate malonates to prepare stabilizers of the invention.

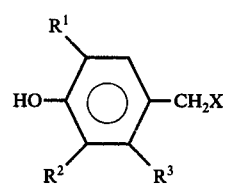

where X equals Cl, Br.

In this case, however, equimolar amounts of alkali metal base must be present per mole of II reacted with the appropriate malonate ester of formula Ic.

The di-lower alkyl malonate ester stabilizers of this invention are readily converted to the higher alkyl malonate ester stabilizers of this invention by transesterification with a higher alcohol, optionally in the presence of a basic catalyst such as sodium methylate, for example as follows:

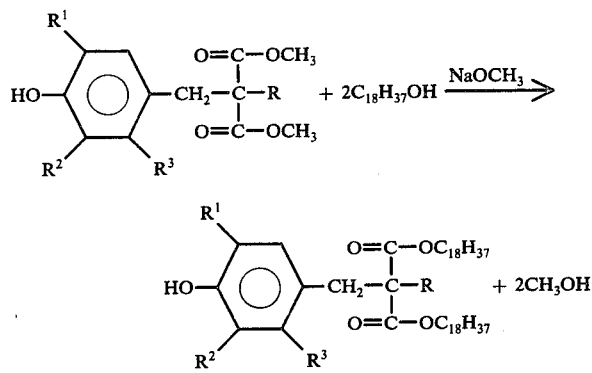

In the above equation, R, $R^1$, $R^2$ and $R^3$ have the same meaning as shown in formula I above.

Listed below are illustrative examples of the compounds of this invention.

diethyl(5-tert.-butyl-2,3-dimethyl-4-hydroxybenzyl)malonate
diisobutyl(5-tert.-amyl-2,3-dimethyl-4-hydroxybenzyl)malonate
di-n-butyl(5-tert.-butyl-2,3-dimethyl-4-hydroxybenzyl)malonate
di-n-dodecyl(5-tert.-butyl-2,3-dimethyl-4-hydroxybenzyl)ethylmalonate
di-n-octadecyl(5-tert.-octyl-2,3-dimethyl-4-hydroxybenzyl)malonate
di-2-ethylhexyl(3,5-diisopropyl-2-methyl-4-hydroxybenzyl)malonate
di-p-tert.-octylphenyl(5-tert.-butyl-2,3-dimethyl-4-hydroxybenzyl)malonate
di-m-tolyl(5-tert.-butyl-2,3-dimethyl-4-hydroxybenzyl)malonate
di-p-dodecylphenyl(5-tert.-butyl-2,3-dimethyl-4-hydroxybenzyl)malonate
di-n-propyl bis(5-tert.-butyl-2,3-dimethyl-4-hydroxybenzyl)malonate
di-n-octyl bis(5-tert.-butyl-2,3-dimethyl-4-hydroxybenzyl)malonate
di-n-eicosyl bis(5-tert.-butyl-2,3-dimethyl-4-hydroxybenzyl)malonate
di-n-triacontyl bis(5-tert.-butyl-2,3-dimethyl-4-hydroxybenzyl)malonate
di-n-dodecyl bis(5-tert.-octyl-2,3-dimethyl-4-hydroxybenzyl)malonate
di-p-tert.-octylphenyl bis(5-tert.-butyl-2,3-dimethyl-4-hydroxybenzyl)malonate
di-cyclohexyl bis(5-tert.-butyl-2,3-dimethyl-4-hydroxybenzyl)malonate.

The compounds of this invention are stabilizers of organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, $\alpha,\beta$-unsaturated acids, $\alpha,\beta$-unsaturated esters, $\alpha,\beta$-unsaturated ketones, $\alpha,\beta$-unsaturated aldehydes and unsaturated hydrocarbons such as butadienes and styrene; poly-$\alpha$-olefins such as high and low density polyethylene, cross-linked polyethylene, polypropylene, poly(4-methylpentane-1 and the like, including copolymers of $\alpha$-olefins; such as ethylene-propylene copolymers, and the like; dienes such as polybutadiene, polyisoprene, and the like, including copolymers with other monomers; polyurethanes such as are prepared from polyols and organic polyisocyanates, and polyamides such as polyhexamethylene adipamide and polycaprolactam; polyesters such as polyethylene terephthalates; polycarbonates such as those prepared from bisphenol-A and phosgene; polyacetals such as polyethylene terephthalate polyacetal; polystyrene, polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(1,2-ethylene)-azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., $\beta$-methoxyethyleneglycol, methoxytriethyleneglycol, triethylene glycol, octaethyleneglycol, dibutyleneglycol, dipropyleneglycol and the like.

The compounds of this invention are particularly useful as UV light stabilizers, especially for the protection of polyolefins, for instance, polyethylene, polypropylene, poly(butene-1), poly(pentene-1), poly (3-methylbutene-1), poly(4-methylpentene-1), various ethylene-propylene and ethylene-propylene diene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfur-containing esters such as distearyl-β-thiodipropionate (DSTDP), dilauryl-β-thiodipropionate (DLTDP) in an amount of from 0.01 to 2% by weight of the organic material, and the like, pourpoint depressants, corrosion and rust inhibitors, dispersing agents, demulsifiers, antifoaming agents, fillers such as glass or other fibers, carbon black, accelerators and the other chemicals used in rubber compounding, plasticizers, color stabilizers, di- and tri-alkyl- and -alkylphenylphosphites, heat stabilizers, ultraviolet light stabilizers, antiozonants, dyes, pigments, metal cholating agents, dyesites and the like. Often combinations such as these, particularly the sulfur containing esters, and phosphites and/or the ultraviolet light stabilizers will produce superior results in certain applications to those expected by the properties of the individual components.

The following formula represents co-stabilizers which are in certain instances very useful in combination with the stabilizers of this invention:

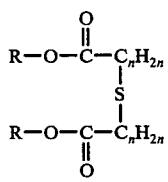

wherein R is an alkyl group having from 6 to 24 carbon atoms; and $n$ is an integer from 1 to 6. Especially useful compounds of this type are dilauryl-β-thiodipropionate and distearyl-β-thiodipropionate. The above co-stabilizers are used in the amount of from 0.01 to 2% by weight of the organic material, and preferably from 0.1 to 1%.

Although the compounds of this invention may to some degree also be effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005 to 5% and preferably from 0.01 to 2% by weight Representative of such antioxidants are phosphite esters, such as triphenylphosphite and dibutylphosphite and alkyl arylphosphites such as dibutylphenylphosphite, and the like.

EXAMPLE 1

6-tert.-butyl-2,3-dimethyl-4-(dimethylaminomethyl)-phenol

To 142.4 grams of 6-tert.-butyl-2,3-dimethylphenol dissolved in 270 ml of toluene was added 144.4 grams of a 25% aqueous solution of dimethylamine at about room temperature. 65.7 Grams of 36.5% aqueous formaldehyde was then added over a 10 minute period to the reaction mixture initially at 15°, the temperature rising to 30° at the end of the addition. The reaction mixture was then warmed to 40° for 3 hours and finally heated at reflux (85°) for 2 hours. The reaction was diluted with about 1 liter of ether and the aqueous layer separated, the upper ether layer being washed three times with water. After drying over sodium sulfate, the organic phase was stripeed to dryness at reduced pressures yielding 176.3 grams of crude product. The crude product was crystallized form heptane, yielding white crystals melting at 101° to 104°.

EXAMPLE 2

6-tert.-octyl-2,3-dimethyl-4-(dimethylaminomethyl)-phenol

This compound was made in substantially the same manner as described in Example 1 by substituting 6-tert.-octyl-2,3-dimethylphenol for the 6-tert.-butyl analog. After trituration from n-hexane, the desired product was obtained as white crystals, melting at 130° to 132° C.

EXAMPLE 3

Dimethyl (5-tert.-butyl-2,3-dimethyl-4-hydroxybenzyl)malonate 1.08 Grams of sodium methylate (0.02 moles) was added to 26.4 grams of dimethylmalonate (0.20 moles) in 25 ml of dry dimethylformamide in a nitrogen atmosphere and warmed to 40° C to obtain a clear solution. 47 grams of 6-tert.-butyl-2,3-dimethyl-4-(dimethylaminomethyl)phenol (0.20 moles) was added at room temperature, the reaction mixture becoming blue and was then gradually heated to 40° C over a period of about 40 minutes during which the blue color disappeared. The reaction mixture was then heated at 80° C for 1¾ hours. After acidification with 6N aqueous hydrochloric acid, the reaction mixture was poured into 200 ml of an ice-water dispersion with stirring to yield a hard crystalline precipitate. This precipitate was taken up in 700 ml of chloroform, the chloroform solution washed successively with dilute hydrochloric acid, water, saturated sodium bicarbonate and finally with water again. After drying over anhydrous sodium sulfate and filtering free of drying agent, the solvent was removed by distillation at reduced pressures. Crystallization of the residue from 1,2-dichloroethane yielded the product as white crystals melting at 140° to 143° C.

EXAMPLE 4

Dimethyl bis(5-tert.-butyl-2,3-dimethyl-4-hydroxybenzyl)malonate 6.6 grams of dimethyl malonate (0.05 moles), 23.5 grams of 6-tert.-butyl-2,3-dimethyl-4-(dimethylaminoaminomethyl)phenol (0.10 moles) and 0.5 grams of sodium methylate were charged to 100 ml of toluene at room temperature and heated at reflux for 4½ hours, dimethylamine being evolved during this period. The reaction mixture cooled to room temperature was made acid with 3N aqueous hydrochloric, the toluene phase being washed with water, the wash water being separated. The desired product was insoluble in the cooled toluene phase and was isolated as white crystals by filtration. After drying and recrystallization from toluene the product melted at 204° to 207° C.

EXAMPLE 5

Di-n-octadecyl(5-tert.-butyl-2,3-dimethylhydroxybenzyl)malonate 0.162 grams of sodium methylate (0.003 moles) was added to 18.27 grams of di-n-octadecyl malonate (10.03 moles) in 150 ml of dimethyl formamide and 50 ml of dry toluene at 45° C to give a clear solution. 7.05 grams of 6-tert.-butyl-2,3-dimethyl-4-(dimethylaminomethyl)-phenol (0.03 moles) dissolved in 30 ml of dry dimethylformamide was added to the di-n-octadecyl malonate solution at 45° to 50° C over a period of about 10 minutes, the yellow reaction mixture being then heated at 50° to 80° C for about 1½ hours, followed by continued heating at 80° C for 2 hours. After acidification with 1 ml of 6N aqueous hydrochloric acid, most of the reaction solvent was removed by distillation at reduced pressure. The residue was poured into water to yield a solid precipitate which was dissolved in about 100 ml of toluene, the toluene solution being washed with water and dried over sodium sulfate. After removal of drying agent by filtration, and the toluene by distillation at reduced pressure, the resulting residue was crystallized from isopropanol to yield the product of this example as white crystals melting at 61° to 63° C.

Di-n-octadecyl(5-tert.-octyl-2,3-dimethyl-4-hydroxybenzyl)malonate was made in a similar manner to that of Example 5 by substituting the intermediate of Example 2 for 6-tert.-butyl-2,3-dimethyl-4-(dimethylaminomethyl)phenol (Example 1).

EXAMPLE 6

6-tert.-butyl-2,3-dimethyl-4-hydroxybenzyl chloride

30 Grams of 6-tert.-butyl-2,3-dimethylphenol dissolved in 100 ml of toluene was added to 2.7 ml of concentrated hydrochloric acid containing 3.3 ml of concentrated sulfuric acid at 5° to 10° C. 26 grams of methylal was added dropwise to the above vigorously stirred dispersion over a period of about 15 minutes after which the reaction mixture was heated at 36° to 37° for 2 hours while bubbling anhydrous gaseous chloride through the reaction mixture. The reaction temperature was allowed to drop to 27° during the following 2 hours while continuing to bubble anhydrous hydrogen chloride thorugh the reaction mixture. The acidic aqueous phase was separated from the reaction mixture after being extracted with toluene and the combined toluene phases washed well with cold water and dried over anhydrous sodium sulfate. After filtering free of drying agent, the clear filtrate was freed of solvent by distillation at reduced pressures the resulting residue being crystallized from petroleum ether yielding the desired compound in the form of light yellow crystals melting at 92° to 95° C.

EXAMPLE 7

Di-n-octadecyl bis(5-tert.-butyl-2,3-dimethyl-4-hydroxybenzyl)malonate

A solution of 6.0 grams of 6-tert.-butyl-2,3-dimethyl-4-hydroxybenzyl chloride (0.025 moles) in 50 ml of toluene is added under nitrogen at room temperature over a period of 20 minutes to a solution of di-n-octadecyl malonate (0.0125 moles) and 2.8 grams of potassium t-butoxide in 125 ml of toluene. The reaction mixture is then heated under nitrogen at 60° to 75°. After the reaction is complete, the reaction mixture is acidified with acetic acid and then washed with 5% sodium bicarbonate and water. After drying the toluene solution and removing the solvent by distillation at a reduced pressure, the product is obtained.

EXAMPLE 8

Di-n-octadecyl bis(5-tert.-butyl-2,3-dimethyl-4-hydroxybenzyl)malonate

The product of this example is made in a similar manner to Example 5 by reacting 2 moles of the intermediate of Example 1 per mole of di-n-octadecyl malonate.

EXAMPLE 9

Unstabilized polypropylene powder (Hercules Profax 6501) is thoroughly blended with 0.2% by weight of diethyl(5-tert.-butyl-2,3-dimethyl-4-hydroxybenzyl)malonate. Also prepared are samples of polypropylene containing 0.1% by weight of the same stabilizer and 0.3% by weight of DSTDP (distearyl-β-thiodipropionate). The blended materials are then milled on a two-roll mill at 182° C for 10 minutes, after which time the stabilized polypropylene is sheeted from the mill and allowed to cool.

The milled polypropylene sheets are then cut into pieces and pressed for 7 minutes on a hydraulic press at 218° C, 2,000 pounds per square inch pressure. The resulting plaques of 25 mil thickness are tested for resistance to accelerated aging in a forced draft oven at 150° C. When the plaques show the first signs of decomposition (e.g., cracking or brown edges) they are considered to have failed. The samples containing said malonate exhibit good resistance to decomposition while the sample containing both the malonate and DSTDP exhibit even better stability.

EXAMPLE 10

Di-n-octadedyl(3,5-dicyclohexyl-2-methyl-4-hydroxybenzyl)malonate is made in a similar manner to Example 5 by substituting 2,6-dicyclohexyl-4-(dimethylaminomethyl)-3-methylphenol for 6-tert.-butyl-2,3-dimethyl-4-(dimethylaminomethyl)phenol.

EXAMPLE 11

Pellets (500 g) of unstabilized nylon-6,6 (Zytel 101, DuPont) are placed in a Kitchen Aid Mixer. With mixing a solution of 0.5% (based on the weight of nylon) di-n-octadecyl(5-t-butyl-2,3-diethyl-4-hydroxybenzyl)malonate in 20 ml of methylene chloride is added slowly. Sodium hypophosphite (0.5 gm 0.1%) is dissolved in 20 ml of water and added slowly with mixing to the nylon pellets after the antioxidant solution has been added and most of the methylene chloride has evaporated. The stabilized pellets are dried at 80° C at <1 mm Hg. for 4 hours.

The polyamide formulation is extruded at 600° F through at ¼ inch die into a rod which is water cooled and chopped into pellets. A ¾ inch Brabender extruder, equipped with a nylon screw, is used. The pellets are dried at 80° C at <1 mm for 4 hours.

The dried pellets are compression molded into 5 mil thick film by pressing at 290° C for 4 minutes at 6,000 psi. The films are oven aged at 150° C in a forced draft oven and samples are removed periodically. The specific viscosity of the samples are determined using a 1% formic acid solution at 25° C. The sample stabilized with the above noted stabilizer required longer aging time to reduce its viscosity by one-half than the unstabilized sample.

EXAMPLE 12

Unstabilized high impact polystyrene resin is dry blended with 0.01% by weight of the resin of di-p-tert.-octylphenyl(5-tert.-butyl-2,3-diethyl-4-hydroxybenzyl)-malonate. The resin is then extrusion compounded on a 1 inch 24/1=L/D extruder melt temperature 500° F and pressed for 7 minutes at a temperature of 163° C and a pressure of 2000 psi into a sheet of uniform thickness of 30 mil. The sheets are then cut into plaques of 2 inch × 2 inch × 30 mil. The plaques are then oven aged at 80° C and color measurements made periodically using a Hunter Color Difference Meter Model D25. The polystyrene samples stabilized with the above stabilizer develops the undesirable yellow discoloration substantially later after such discoloration occured in the unstabilized samples.

EXAMPLE 13

Unstabilized linear polyethylene (HiFax 4401) is solvent blended in methylene chloride with 0.02% by weight of the substrate of di-n-octadecyl(5-tert.-octyl-2,3-dimethyl-4-hydroxybenzyl)malonate and then vacuum dried. The resin is then extruded at 550° F using a ¾ inch extruder having 5 times 24:1 L/D ratio. The melt flow rate of a sample of the resin is determined after each extrusion according to ASTM test D-1238. Polyethylene stabilized with above compound is found to undergo less change in the melt flow rate than the unstabilized polyethylene.

What is claimed is:

1. Compounds having the formula

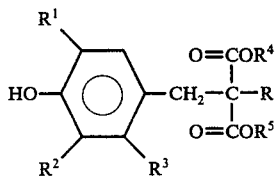

wherein $R^1$, $R^2$ and $R^3$ are independently alkyl groups of 1 to 8 carbons, $R^4$ and $R^5$ are alkyl of 1 to 30 carbons, phenyl, alkyl substituted phenyl having up to 24 carbons, or cyclohexyl, and R is hydrogen, alkyl of 1 to 8 carbons or a group

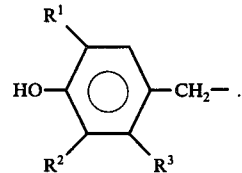

2. A compound of claim 1 wherein
$R^1$ is branched alkyl,
$R^2$ and $R^3$ are alkyl of 1 to 3 carbons,
$R^4$ and $R^5$ are alkyl of 1 to 18 carbons, and
R is hydrogen or the group

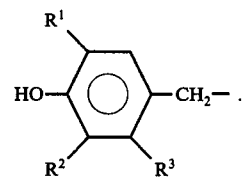

3. A compound of claim 2 wherein
$R^1$ is tert-butyl, and
$R^2$ and $R^3$ are methyl.

4. The compound of claim 1 which is di-n-octadecyl(5-tert.-butyl-2,3-dimethylhydroxybenzyl)malonate.

5. The compound of claim 1 which is di-n-octadecyl bis(5-tert.-butyl-2,3-dimethyl-4-hydroxybenzyl)malonate.

6. The compound of claim 1 which is dimethyl (5-tert.-butyl-2,3-dimethyl-4-hydroxybenzyl)malonate.

7. The compound of claim 1 which is dimethyl bis(5-tert.-butyl-2,3-dimethyl-4-hydroxybenzyl)malonate.

* * * * *